United States Patent [19]

Takase

[11] Patent Number: 5,248,297
[45] Date of Patent: Sep. 28, 1993

[54] SUCTION TUBE FOR USE IN SURGICAL OPERATION

[76] Inventor: Haruo Takase, 20-16, Shimoochiai 3-chome, Tokyo, Japan, 161

[21] Appl. No.: 910,499

[22] Filed: Jul. 8, 1992

[30] Foreign Application Priority Data

Feb. 27, 1992 [JP] Japan .................................. 4-18093

[51] Int. Cl.⁵ .............................................. A61B 17/32
[52] U.S. Cl. .................................... 604/22; 604/902
[58] Field of Search ................. 604/35, 43, 45, 19, 604/22, 902

[56] References Cited

U.S. PATENT DOCUMENTS

| | | | |
|---|---|---|---|
| 1,114,268 | 10/1914 | Kells | 604/902 |
| 2,449,497 | 9/1948 | McLeod | 604/45 |
| 3,810,471 | 5/1974 | Truhan | 604/902 |
| 4,002,170 | 1/1977 | Hansen et al. | 604/902 |
| 4,648,871 | 3/1987 | Jacob | 604/149 |
| 4,650,461 | 3/1987 | Woods | 604/28 |
| 4,690,672 | 9/1987 | Veltrup | 604/43 |
| 4,808,157 | 2/1989 | Coombs | 604/44 |
| 4,850,354 | 7/1989 | McGurk-Burleson | 604/22 |
| 4,861,332 | 8/1989 | Parisi | 604/22 |
| 4,872,837 | 10/1989 | Issalene et al. | 433/29 |
| 4,886,491 | 12/1989 | Parisi et al. | 604/22 |
| 4,900,300 | 2/1990 | Lee | 604/22 |
| 4,913,698 | 4/1990 | Ito et al. | 604/22 |
| 4,958,901 | 9/1990 | Coombs | 604/44 |
| 5,047,008 | 9/1991 | Juan, Jr. | 604/22 |
| 5,084,013 | 1/1992 | Takase | 604/43 |
| 5,112,299 | 5/1992 | Pascaloff | 604/22 |

FOREIGN PATENT DOCUMENTS

| | | |
|---|---|---|
| 0331313 | 9/1989 | European Pat. Off. . |
| 2447513 | 4/1976 | Fed. Rep. of Germany . |
| 8709667 | 10/1987 | Fed. Rep. of Germany . |
| 2454308 | 11/1980 | France . |
| 2-94554 | 7/1990 | Japan . |

*Primary Examiner*—Paul J. Hirsch
*Attorney, Agent, or Firm*—Wenderoth, Lind & Ponack

[57] ABSTRACT

A surgical suction tube has a relief path formed between a suction tube body for sucking subcutaneous tissues through a suction mouth and a fluid supply tube for supplying a fluid such as Ringer's solution around the suction mouth. Since the fluid sent through the fluid supply tube is permitted to flow into the suction tube body through the relief path, it is in no way blocked even when the fluid supply tube is closed with subcutaneous tissues, and consequently the surgical operation can be continuously performed without interruption.

6 Claims, 3 Drawing Sheets

FIG_1
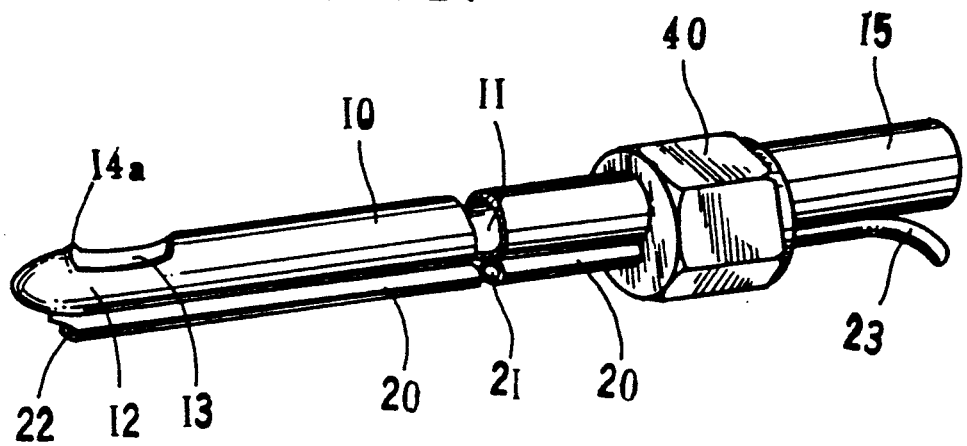
FIG_2
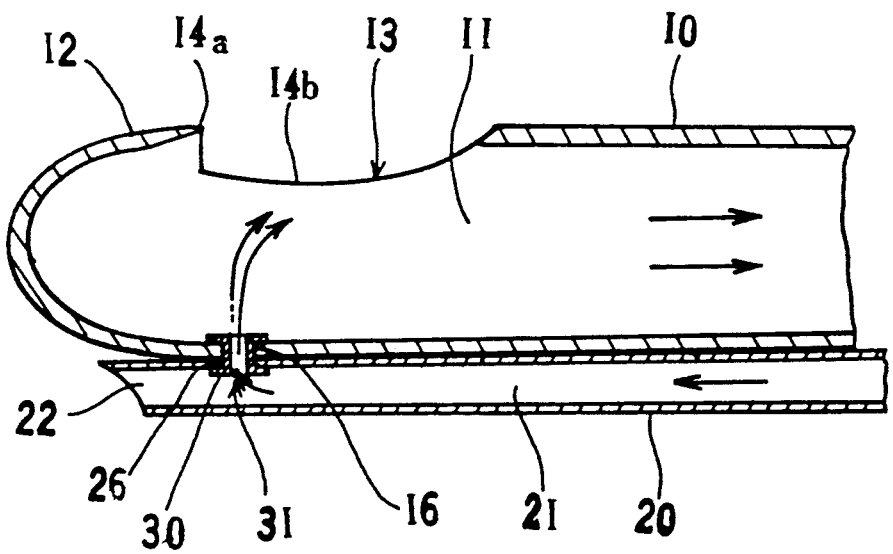

FIG_3
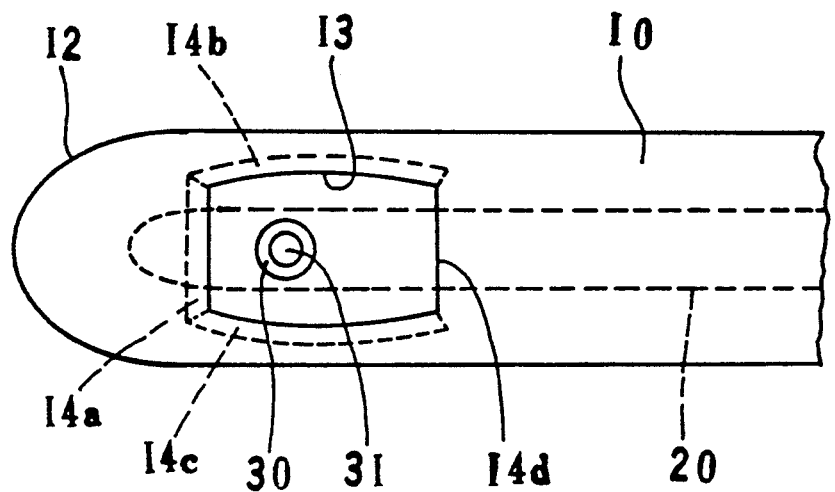
FIG_4
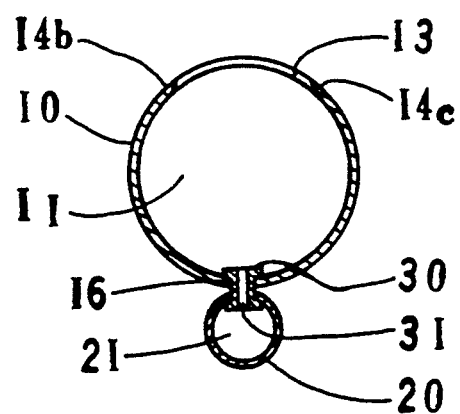

FIG_5
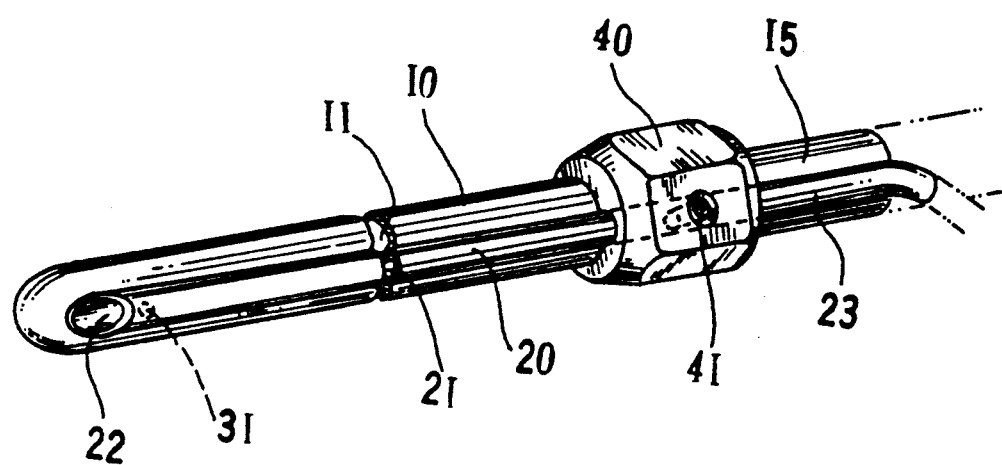

SUCTION TUBE FOR USE IN SURGICAL OPERATION

BACKGROUND OF THE INVENTION

1. Field of the Invention

This invention relates to a suction tube for use in a surgical operation such as plastic surgery for aspirating subcutaneous fat or other tissues, and more particularly, to an improvement in and concerning a surgical suction tube with which a surgical operation for fat aspirating or other purposes can be performed readily and safely and which is expected to reduce the period for healing an operation wound.

2. Description of the Prior Art

Among the various types of surgical suction tubes used in a surgical operation for aspirating subcutaneous fat or other tissues, typical is that disclosed in U.S. Pat. No. 5,084,013 issued on Jan. 28, 1992 to Haruo Takase, the inventor of this invention. The surgical suction tube earlier proposed by the inventor is now finding widespread acceptance for actual use in a surgical operation. This conventional suction tube comprises a suction tube body provided at its leading end portion with a suction mouth, and a fluid supply tube for supplying a fluid such as air and Ringer's solution around the suction mouth. The suction mouth in the suction tube body opens in a direction different from the axial direction of the suction tube body. The fluid supply tube is attached to the outside of the suction tube body in parallel. This suction tube has an advantage in that it can aspirate the subcutaneous fat or the like in plastic surgery with notably high efficiency in safety and enjoys higher operability in comparison with other conventional suction tubes.

However, there is a possibility that such subcutaneous tissues enter into the leading end outlet of the fluid supply tube, thereby preventing the spouting of fluid such as Ringer's solution. As a result, the efficiency of aspirating the subcutaneous fat or the like is lowered. Therefore, in such a case, it is required to discontinue performing the operation to clean the fluid supply tube every time the fluid supply tube is blocked. Thus, the conventional suction tube entailed a disadvantage such that the work of removing the blockage tissues in the fluid supply tube takes much time and labor and proves to be troublesome, whereby the surgical operation is prolonged.

Furthermore, the conventional surgical suction tubes including the aforenoted suction tube generally have a function of taking subcutaneous fat or other tissues off by dint of only a sucking force, but sufficient effect of aspirating such tissues could not be obtained. Thus, a need has been felt for a suction tube capable of easily sucking out the subcutaneous fat or other tissues with high efficiency.

OBJECTS OF THE INVENTION

This invention was made to eliminate the drawbacks suffered by the conventional surgical suction tubes and aims at offering a surgical suction tube capable of effectively sucking out tissues such as subcutaneous fat and enabling a surgical operation such as plastic surgery to be continuously performed without a break even when a fluid supply tube is blocked with the tissues.

Another object of this invention is to provide a surgical suction tube capable of freely cutting off subcutaneous tissues while sucking out the tissues.

SUMMARY OF THE INVENTION

To attain the objects described above according to the present invention there is provided a surgical suction tube comprising a suction tube body having a suction mouth opening in a direction different from the axial direction of the suction tube body, and a fluid supply tube attached outside the suction tube body so as to permit a fluid to be supplied toward around the suction mouth of the suction tube body, which suction tube body and fluid supply tube have portholes mutually joined to form a relief path between the fluid supply tube and the suction tube body.

A fluid such as Ringer's solution which is supplied through the fluid supplied tube is permitted to pass through the relief path from the fluid supply tube to the suction tube body in performing a surgical operation for aspirating subcutaneous fat, for example. The great part of fluid supplied through the fluid supply tube is discharged from the leading end outlet of the fluid supply tube around the suction mouth formed in the suction tube body under normal conditions. However, when the leading end outlet is blocked with tissues or the like, the fluid sent through the fluid supply tube flows into the suction tube body through the relief path. As a result, the surgical operation can be continued without a break.

By providing at least a part of the edge of the suction mouth with cutting means, the subcutaneous tissues can be easily cut off by moving the suction tube body in its lengthwise direction or rotating the suction tube body from side to side while sucking out the tissues.

Other and further objects of this invention will become obvious upon an understanding of the illustrative embodiments about to be described or will be indicated in the appended claims, and various advantages not referred to herein will occur to one skilled in the art upon employment of the invention in practice.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 1 is a perspective view showing one embodiment of the surgical suction tube according to this invention;

FIG. 2 is a sectional side view of the same;

FIG. 3 is a plan view of the same;

FIG. 4 is a sectional front view of the same; and

FIG. 5 is a perspective view showing another embodiment of the present invention.

DESCRIPTION OF THE PREFERRED EMBODIMENT

The surgical suction tube according to this invention comprises, as illustrated in FIGS. 1 through 4 as a first embodiment, a cylindrical suction tube body 10 having a suction passage 11, and a cylindrical fluid supply tube 20 having a fluid supply passage 21.

A head portion 12 at the leading end part of the suction tube body 10 is closed in the form of a hemisphere and has a suction mouth 13 which opens in a direction different from or substantially perpendicular to the axial direction of the suction tube body 10. Along the edge of the suction mouth 13, there is formed cutting means 14.

In this embodiment, the suction mouth 13 in the suction tube body 10 is shaped substantially in a rectangle having long lengthwise sides 14b and 14c and short circumferential sides 14a and 14d, as illustrated in FIG. 3. However, the shape of the suction mouth 13 is not specifically limited, and any other desired shape such as a circle, ellipse and triangle may be chosen.

Although the cutting blades serving as the cutting means 14 are formed at the sides 14a, 14b and 14c, the rear side 14d is also provided with a cutting blade as a matter of course.

The fluid supply tube 20 is smaller in diameter than the suction tube body 10 and attached integrally onto the outer circumferential surface of the suction tube body 10 by welding or by using an adhesive agent. The fluid supply tube 20 opens at its leading end to form a fluid outlet 22. The fluid outlet 22 is aslant as if cut by a slant plane, preferably, tangential to the spherical surface of the leading end of the head portion 12 of the suction tube body 10.

The suction tube body 10 and fluid supply tube 20 are supported at their basal end by a retaining member 40.

In the circumferential side of the suction tube body 10, a porthole 16 is formed, and correspondingly, in the circumferential side of the fluid supply tube 20 is formed a porthole 26. These portholes 16 and 26 are mutually joined to form a relief path 31. In actuality, the relief path 31 is secured by fitting an eyelet member 30 into the joined portholes 16 and 26.

The suction tube body 10 and fluid supply tube 20 are connected to an aspirator (not shown) or any other apparatuses through respective conduits 15 and 23.

In using the surgical suction tube described above for performing a surgical operation, the head portion 12 of the suction tube body 10 is inserted under the skin of a patient through an incision in the skin. The inner pressure of the suction tube body 10 is reduced by driving the aspirator while supplying air or Ringer's solution around the suction mouth 13 through the fluid supply tube 20, so that subcutaneous tissues such as fat can be effectively sucked out through the suction passage 11 and conduit 15. At the time of sucking the subcutaneous tissues by dint of the sucking force supplied inside the suction tube body 10, by moving or rotating the suction tube inserted under the skin, the subcutaneous tissues can be partially cut off by the cutting blades 14a–14c formed at the edges of the suction mouth 13 and effectively removed through the suction tube body 10. In this case, the suction tube may be moved back and forth or rolled from side to side to cut off the tissues.

The skin and subcutaneous tissues may possibly be injured by: particularly the cutting blade 14a formed at the front edge of the suction mouth 13 when the suction tube body 10 is drawn out straight from the skin. However, by drawing out the suction tube body 10 while lightly depressing the head portion 12 downward, the skin and other tissues are not needlessly injured.

When fluid outlet 22 of fluid supply tube 20 is closed with the tissues in the midst of performing the plastic surgery for aspirating the subcutaneous tissues, fluid such as Ringer's solution sent through the fluid supply passage 21 flows into the suction passage 11 inside the suction tube body 10 through the relief path 31, so that the tissues teared by suction can be smoothly sent out through the suction passage 11 so that the surgical operation can be performed without a break.

It is desired to make the relief path 31 sufficiently small so as not to decrease the efficiency of suction produced when the fluid supply tube 20 is not blocked. That is, the relief path 31 should be so designed as to prevent the fluid sent through the fluid supply passage 21 from flowing into the suction passage 11 through the relief path 31 serving as a short-circuit path under normal conditions. Otherwise, a safety valve, relief valve or the like may be mounted in the relief path 31 so that the fluid such as Ringer's solution is permitted to pass through the relief path 31 only when the pressure inside the fluid supply tube 20 is raised.

Though the suction tube of the foregoing embodiment has the cutting blade at the edge portions of the suction mouth 13, the cutting blade is not absolutely necessary to this invention. Also, the structure according to this invention can be applied to a surgical suction tube using ultrasonic vibration.

FIG. 5 illustrates a second embodiment of the surgical suction tube according to this invention, in which a finger hole 41 is formed in the retaining member 40 so as to be closed with the finger tip of an operator. The finger hole 41 communicates with the fluid supply passage 21 of the tube 20. In this figure, the elements depicted by like reference numerals with respect to those of the first embodiment described above have analogous structures and functions to those of the first embodiment and will not be described in detail again.

When the finger hole 41 is closed by the finger tip, the air supplied via the conduit means 23 entirely flows out from the fluid outlet 22. Meanwhile, when the finger hole 41 is open, the air from the conduit means 23 is released through the finger hole 41 in greater or lesser amounts Thus, by opening and closing the finger hole 41 with the finger tip, while performing a surgical operation for aspirating tissues such as subcutaneous fat while supplying the air around the leading end portion of the suction tube body 10, the quantity of the supplied air can be appropriately controlled.

There are times when the subcutaneous tissues are aspirated only by the suction force brought about within the suction tube body 10 without supplying any fluid such as air and a Ringer's solution. In this case, the finger hole 41 may be operated with the finger tip so as to permit the air to be introduced into the fluid supply passage 21 and supplied around the leading end portion of the suction tube body 10 with the attraction acted in the suction passage 11. Thus, by suitably controlling the finger hole 41 with the finger tip, the subcutaneous tissues can be effectively aspirated. Moreover, when the suction mouth 13 or suction passage 11 is obstructed by fragments of subcutaneous tissue, the opening and closing operations of the finger hole 41 are performed many times to vary the suction force in the suction passage 11, thereby imparting shocks to the obstacles of the subcutaneous tissues. Consequently, in the meantime, the obstacles are removed.

When the fluid such as the Ringer's solution is supplied, the finger hole 41 may be plugged with a stopper or bound fast with a rubber band or the like.

As is readily understood from the above, since the suction tube according to this invention has a suction mouth opening in a direction perpendicular to the axial direction, the subcutaneous tissues can be sucked out with high efficiency without needlessly injuring blood vessels and nerve tissues. The suction tube of this invention has further a cutting blade formed at a part of the edge portion of the suction mouth, so that the subcutaneous tissues can be effectively cut and readily removed by moving back and forth or rotating from side to side the suction tube inserted under the skin.

Furthermore, since the suction tube of this invention is provided with a relief path between a suction tube body and fluid supply tube, the fluid flowing through the fluid supply tube is not blocked even when the fluid supply tube is closed with the tissues, so that the surgical operation can be continuously performed without a break. Besides, by providing the fluid supply tube with a finger hole capable of closing with the finger tip of an operator, air or other fluid to be supplied around the leading end portion of the suction tube body can be easily and appropriately controlled.

It is to be understood that the invention is not limited in its application to the details of construction and arrangement of parts illustrated in the accompanying drawings, since the invention is capable of other embodiments and of being practiced or carried out in various ways. Also it is to be understood that the phraseology or terminology employed herein is for the purpose of description and not of limitation.

What is claimed is:

1. A surgical suction tube, comprising:
    a suction tube body having a suction mouth opening defined by at least one side edge portion having a cutting blade, said suction mouth opening being directed in a direction substantially perpendicular to the axial direction of said suction tube body;
    a fluid supply tube defining a fluid supply passage attached to the outside of said suction body and having, at its leading end, a fluid outlet which is substantially aslant along a plane slanted relative to the axial direction of said suction tube body so as to be capable of supplying fluid toward and around said suction mount of said suction tube body; and
    portholes provided in said suction tube body and said fluid supply tube, said portholes being connected to each other so as to define a relief path allowing the fluid to at least partly flow from said fluid supply passage to said suction tube body.

2. The surgical suction tube of claim 1, wherein said fluid supply tube further has a finger hole therein capable of being closed by a finger tip.

3. The surgical suction tube of claim 1, wherein said suction tube body and said fluid supply tube are commonly supported at basal ends thereof by a retaining member, said retaining member having a finger hole therein communicating with said fluid supply passage and capable of being closed by a finger tip.

4. The surgical suction tube of claim 1, wherein said suction mount opening is substantially rectangular in shape, having long sides extending in the axial direction of said suction tube body and short sides at front and rear sides of said suction mouth, said at least one side edge portion having said cutting blade comprising said short side at the front side of said suction mouth and said long sides.

5. The surgical suction tube of claim 1, wherein said portholes are connected to each other by, and said relief path is defined by, an eyelet member fitted into said portholes.

6. The surgical suction tube of claim 1, wherein said suction tube body has a hemispherical end forward of said suction mouth opening, said plane slanting substantially tangential to said hemispherical end.

* * * * *